United States Patent
Fagan et al.

(10) Patent No.: US 7,153,996 B2
(45) Date of Patent: Dec. 26, 2006

(54) PREPARATION OF LEVULINIC ACID ESTERS AND FORMIC ACID ESTERS FROM BIOMASS AND OLEFINS

(75) Inventors: Paul Joseph Fagan, Wilmington, DE (US); Leo Ernest Manzer, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 755 days.

(21) Appl. No.: 10/404,322

(22) Filed: Apr. 1, 2003

(65) Prior Publication Data

US 2003/0233011 A1 Dec. 18, 2003

Related U.S. Application Data

(60) Provisional application No. 60/369,380, filed on Apr. 1, 2002.

(51) Int. Cl.
*C07C 69/66* (2006.01)
*C07C 67/04* (2006.01)

(52) U.S. Cl. ...................................... 560/174; 560/247
(58) Field of Classification Search ...................... None
See application file for complete search history.

(56) References Cited

U.S. PATENT DOCUMENTS

| | | | |
|---|---|---|---|
| 2,033,909 A | 3/1936 | Cox et al. | |
| 3,489,795 A | 1/1970 | Gal et al. | |
| 5,608,105 A | 3/1997 | Fitzpatrick | |
| 5,859,263 A | 1/1999 | Ghorpade et al. | |
| 6,054,611 A | 4/2000 | Farone et al. | |

FOREIGN PATENT DOCUMENTS

WO  WO 94/21753  9/1994

OTHER PUBLICATIONS

Olson et al, Levulinate Esters from Biomass Wastes, Book of Abstracts, 218th ACS National Meeting, New Orleans, Aug. 22-26, 1999, CELL-013.*

Edwin S. Olson, Michelle R. Kjelden, Adam J. Schlag and Ramesh K. Sharma, Levulinate Esters from Biomass Wastes, American Chemical Society, p. 51-63, 2001.

* cited by examiner

*Primary Examiner*—Paul A. Zucker

(57) ABSTRACT

This invention relates to a process for producing a mixture of levulinic acid esters and formic acid esters from biomass and olefins, and the composition prepared therefrom. This invention also relates to usage of the mixture of these esters as fuel and as fuel additives for gasoline fuel, diesel fuel, and biofuel.

17 Claims, 2 Drawing Sheets

Fuel Additive Characteristics of Ester Oxygenates Made by the Process of the Invention – Comparative Data

| Fuel Additive Characteristic | O₂ Content (wt %) | Content in Oxygenated Gasoline (wt %) | Content in Oxygenated Gasoline (wt %) | Vapor Pressure at 100°F (kPa) | Blending Octane No. (R+M)/2 |
|---|---|---|---|---|---|
| Additive Name | | 2.7 wt% O₂ Requirement | 2.0 wt% O₂ Requirement | [1] | As Reported |
| MTBE | 18 | 11 | 14.9 | 55 | 109 [2] |
| Methyl Formate | 53 | 3.8 | 5.1 | 126.2 | 101.5 [3] |
| Ethyl Formate | 43 | 4.6 | 6.3 | 55 | 102.5 [3] |
| N-Propyl Formate | 36 | 5.5 | 7.4 | 19.9 | |
| Isopropyl Formate | 36 | 5.5 | 7.4 | 7.4 | |
| N-Butyl Formate | 31 | 6.4 | 8.6 | 10.2 | |
| Isobutyl Formate | 31 | 6.4 | 8.6 | 12.1 | |
| Sec-Butyl Formate | 31 | 6.4 | 8.6 | 19.8 | |
| Tert-Butyl Formate | 31 | 6.4 | 8.6 | 19.8 | |
| Amyl Formate Ester | 28 | 7.3 | 9.8 | 2.5 | |

FIG. 1A

Fuel Additive Characteristics of Ester Oxygenates Made by the Process of the Invention - Comparative Data

| Fuel Additive Characteristic | O₂ Content (wt %) | Content in Oxygenated Gasoline (wt %) | Content in Oxygenated Gasoline (wt %) | Vapor Pressure at 100°F (kPa) | Blending Octane No. (R+M)/2 |
|---|---|---|---|---|---|
| Additive Name | | 2.7 wt% O₂ Requirement | 2.0 wt% O₂ Requirement | [1] | As Reported |
| Methyl Levulinate | 37 | 5.4 | 7.3 | | 106.5[3] |
| Ethyl Levulinate | 33 | 6.6 | 8.1 | | 107.5[3] |
| N-Propyl Levulinate | 30 | 6.6 | 8.9 | | |
| Isopropyl Levulinate | 30 | 6.6 | 8.9 | | 105[3] |
| N-Butyl Levulinate | 28 | 7.2 | 9.7 | | |
| Isobutyl Levulinate | 28 | 7.2 | 9.7 | | 102.5[3] |
| Sec-butyl Levulinate | 28 | 7.2 | 9.7 | | 102.5[3] |
| Tert-Butyl Levulinate | 28 | 7.2 | 9.7 | | |
| Amyl Levulinate | 26 | 7.8 | 10.5 | | |
| Isoamyl Levulinate | 26 | 7.8 | 10.5 | | |

FIG. 1B

PREPARATION OF LEVULINIC ACID ESTERS AND FORMIC ACID ESTERS FROM BIOMASS AND OLEFINS

CROSS-REFERENCE TO RELATED APPLICATION

This application claims the benefit of the filing date of provisional application Ser. No. 60/369,380, filed Apr. 1, 2002.

FIELD OF INVENTION

This invention relates to a process for producing a mixture of levulinic acid esters and formic acid esters from biomass and olefins, and the composition produced therefrom. This invention also relates to usage of the mixture of these esters as fuel and fuel additives for gasoline fuel, diesel fuel, and biofuel.

BACKGROUND OF THE INVENTION

"Fuel additives" are substances that can improve the fuel efficiency of an engine for example, as measured by the octane number, the cetane number or any other index suited to measure the efficiency of a particular fuel. A fuel additive also performs the function of lubricating, cleaning and stabilizing the fuel. Further, a fuel additive can also improve performance, economy, and injector life and reduce emissions and smoke related to an engine. A fuel additive can also help eliminate tank draining. A fuel additive can also possibly lower a gel point of the fuel in question. It can also provide a clean burning fuel that can inhibit polluting agents in emissions. These are a few examples of the functions of fuel additives and not a comprehensive or an exhaustive list. The compositions of the invention are intended for use as desirable fuel additives.

"Oxygenates" is a commonly referred to group of chemical compounds that raise the oxygen content of gasoline. Oxygen helps gasoline burn more completely, reducing harmful tailpipe emissions from motor vehicles. In one respect, the oxygen dilutes or displaces gasoline components such as aromatics (e.g., benzene), and sulfur. Additionally, it optimizes oxidation during combustion. Most gasoline suppliers meet the oxygen content requirements of the different clean fuel programs by adding oxygenate fuel additives, most commonly, methyl tertiary-butyl ether, (hereinafter referred to as MTBE) to gasoline blend stocks. Recently, various environmental protection agencies have begun raising concerns regarding the detection of MTBE in surface and ground water.

A need exists to develop esters with low water solubility that could be used to meet governmental oxygen requirements for gasoline and oxy-gasoline fuels. These low solubility esters would have a reduced solubility in surface and subsurface water and could therefore reduce the impact on such waters from spills and emissions of oxygenated fuels. It would also be desirable for MTBE replacements, including these esters, to have other favorable properties such as low ozone formation potential and a low rubber seal-swelling tendency.

The present invention relates to a gasoline fuel, diesel fuel or a biofuel comprising mixed esters as fuel additives, wherein the ester contains 2 to 22 carbon atoms. This invention also relates to a process of producing a mixture of levulinic acid esters and formic acid esters from biomass and olefins. It is believed that some of the compositions of esters of the invention have low water solubility. This invention further relates to using the compositions of esters as oxygenates in automotive gasoline used in internal combustion engines, as oxygenates in diesel engines, and as additives to biofuel. The invention also relates to the use of the esters as octane number-enhancing agents for gasoline, and as cetane number-enhancing agents in diesel fuels.

Levulinic acid is used to make resins, plasticizers, specialty chemicals, herbicides, and methyl tetrahydrofuran, which is used as a fuel extender, as a pharmaceutically active compound, and as a flavor substance. Levulinic acid is useful as a solvent, and as a starting material in the preparation of a variety of industrial and pharmaceutical compounds such as diphenolic acid (useful as a component of protective and decorative finishes), calcium levulinate (a particularly suitable form of calcium for intravenous injection used for calcium replenishment and for treating hypocalcemia, (see Cox et al., U.S. Pat. No. 2,033,909)). The use of the sodium salt of levulinic acid as a replacement for ethylene glycols as an antifreeze has also been proposed. Esters of levulinic acid are known to be useful as plasticizers and solvents, and have been suggested as fuel additives. Acid catalyzed dehydration of levulinic acid yields alpha-angelica lactone, which has been shown to increase octane ratings. Olson, E. S., et al., "Levulinate Esters from Biomass Wastes," ACS Symposium Series, 784, 2001. Levulinic acid has been synthesized by a variety of chemical methods. But levulinic acid has not attained much commercial significance due in part to the high cost of the raw materials needed for synthesis. Another reason is the low yields of levulinic acid obtained from most synthetic methods. Yet, another reason is the formation of a formic acid byproduct during synthesis and its separation from the levulinic acid. Therefore, the production of levulinic acid has had high associated equipment costs. Despite the inherent problems in the production of levulinic acid, however, the reactive nature of levulinic acid makes it an ideal intermediate leading to the production of numerous useful derivatives.

Cellulose-based biomass, which is an inexpensive feedstock, is now used as a raw material for making levulinic acid. The supply of sugars from cellulose-containing plant biomass is immense and replenishable. Most plants contain cellulose in their cell walls. For example, cotton comprises 90% cellulose. Furthermore, it has been estimated that roughly 75% of the approximate 24 million tons of biomass generated on cultivated lands and grasslands are waste. The cellulose derived from plant biomass can be a suitable source of sugars to be used in the process of obtaining levulinic acid. Thus, the conversion of such waste material into a useful chemical, such as levulinic acid, would be desirable. Moreover, it would be most desirable to be able to produce levulinic acid in an economically viable and environmentally safe process. Levulinic acid production from biomass is briefly described in the processes of following U.S. patents.

U.S. Pat. No. 5,859,263 describes a process for producing levulinic acid by extrusion of mixture of starch, water and mineral acid in a screw extruder. Mineral acids that have been used are hydrochloric acid, hydrobromic acid, or sulfuric acid. The starch has an amylose content of 20–30%. The starch is obtained from corn, wheat, rice, tapioca, or mixtures thereof. The process is carried out in the temperature range of 80° C. to 150° C. Before the levulinic acid can be used for any of the purposes outlined above, it has to be separated out from the extrudate in a series of process steps.

The separation is accomplished by partial neutralization, filtration/vacuum steam distillation, or solvent extraction. In a preferred embodiment, the extrudate is filter pressed, and the resulting filtrate is subjected to steam distillation. The discharge product of the distillation containing levulinic acid is condensed and centrifuged. Some, or all of the liquor discharged from the centrifugation is recycled to the pre-conditioning zones of a twin screw extruder.

U.S. Pat. No. 5,608,105 describes a process for producing levulinic acid by hydrolyzing a dilute concentration of carbohydrate-containing material in a mineral acid at temperatures in the range of 210° C. to 230° C. Hydroxymethylfurfural, along with other reaction intermediates are formed in this step. The products of this step are further hydrolyzed in presence of a mineral acid in the temperature range of 195–215° C. to give levulinic acid. This process gives levulinic acid in 60%–70% yield of the theoretical limit. Carbohydrate containing materials used for the process are waste paper sludge, raw wood flour, recycled paper sludge, wood paper sludge, and cellulose containing materials. In the second step, the process conditions are adjusted such that furfural and formic acid thus produced are vaporized and externally condensed. The levulinic acid settles at the bottom of the second reactor vessel. The conditions are adjusted such that any furfural and formic acid vaporize quickly.

U.S. Pat. No. 6,054,611 describes production of levulinic acid from sugars produced as a result of strong acid hydrolysis of biomass. The steps of this method include: 1) mixing biomass containing cellulose and hemicellulose with a solution of approximately 5–50% acid, preferably 10–30% acid, thereby decrystallizing the biomass, 2) heating the mixture to about 80–200° C., preferably 110–160° C., for 1 to 30 hours, preferably 2 to 10 hours, thereby hydrolyzing the cellulose and hemicellulose materials and causing the reaction of the resulting mixture of sugars to form the reaction products, 3) pressing or filtering to separating the liquid portions from the solid biomass portion, 4) separating the reaction products, and 5) recovering levulinic acid. It is preferred that the reaction products be filtered prior to separation. Additionally, it is preferable that the filter is washed one or two times and that preferably these washes are to be combined prior to separation. Moreover, following separation of the reaction products, levulinic acid can be concentrated to facilitate any further reaction.

As evident from the above-described methods, a major problem with using levulinic acid is the separation of pure levulinic acid from the byproducts, especially from formic acid. The present invention addresses the problem by describing a process which makes it unnecessary to separate out the formic acid, but instead produces a mixture of acid esters, which can be used as oxygenate additives to fuels, having superior oxygenate quality as compared to levulinic acid ester. Additionally, the ester formation process facilitates separation of the organic phase consisting of fuel additives from the aqueous phase.

SUMMARY OF THE INVENTION

Disclosed herein is a process for preparing a mixture of levulinic acid esters and formate esters from biomass, comprising the steps of:
(a) contacting the biomass with water in the presence of a first acid catalyst to form a first reaction mixture comprising levulinic acid, formic acid and furfural, the first reaction mixture having a liquid phase and, optionally, a solid phase;
(b) optionally, separating the liquid phase from the solid phase of the first reaction mixture to form a second reaction mixture;
(c) removing the furfural from the first reaction mixture or the second reaction mixture to form a third reaction mixture;
(d) contacting the first reaction mixture, the second reaction mixture, or the third reaction mixture with at least one olefin, optionally, in the presence of a second acid catalyst, to produce a fourth reaction mixture, the fourth reaction mixture having an organic phase and an aqueous phase;
(e) separating the organic phase containing levulinic acid esters and formic acid esters from the aqueous phase of the fourth reaction mixture; and
(f) optionally, isolating the mixture comprising levulinic acid esters and formic acid esters from the organic phase of step (e).

Also disclosed are compositions comprising levulinic acid esters and formate esters produced by the process of the invention. Also disclosed is the use of the compositions of the invention as a fuel and as fuel additives to gasoline, diesel and biofuel, as oxygenates, and as octane- and cetane-enhancing agents.

DRAWING

FIG. 1 is a table showing the comparative data of fuel additive characteristics of the compositions of the invention as compared to methyl tertiary-butyl ether (MTBE).

DETAILED DESCRIPTION OF THE INVENTION

As used herein, the term "biomass" refers to a primarily carbohydrate-containing material. Biomass can also refer to a polysaccharide-containing material. It can also refer to a cellulose-, hemicellulose-, or lignocellulose-containing material. Biomass is commonly obtained from, for example, wood, plants, residue from agriculture or forestry, organic component of municipal and industrial wastes, primary sludges from paper manufacture, waste paper, waste wood (e.g., sawdust), agricultural residues such as corn husks, corn cobs, rice hulls, straw, bagasse, starch from corn, wheat oats, and barley, waste plant material from hard wood or beech bark, fiberboard industry waste water, bagasse pity, bagasse, molasses, post-fermentation liquor, furfural still residues, aqueous oak wood extracts, rice hull, oats residues, wood sugar slops, fir sawdust, naphtha, corncob furfural residue, cotton balls, rice, straw, soybean skin, soybean oil residue, corn husks, cotton stems, cottonseed hulls, starch, potatoes, sweet potatoes, lactose, waste wood pulping residues, sunflower seed husks, hexose sugars, pentose sugars, sucrose from sugar cane and sugar beets, corn syrup, hemp, and combinations of the above.

"Levulinic acid" as used herein means a compound having the following formula:

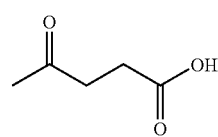

"Formic acid" as used herein means a compound having the following formula:

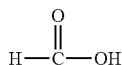

"Levulinic acid ester" of the invention means an ester having the following formula, wherein $R_5$ is a linear, branched, cyclic or bicyclic hydrocarbyl group with a total number of carbon atoms being not more than twenty two.

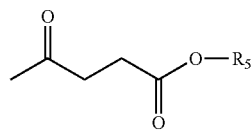

"Formic acid ester" of the invention means an ester having the following formula, wherein $R_5$ is a linear, branched, cyclic or bicyclic hydrocarbyl group with a total number of carbon atoms being not more than twenty two.

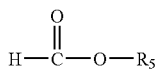

Preferred levulinic acid esters and formic acid esters of the invention are those wherein $R_5$ can be a linear, branched, cyclic or bicyclic hydrocarbyl group with total number of carbon atoms not more than nine.

"Olefin" herein means a compound having the following general formula:

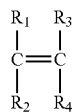

wherein $R_1$, $R_2$, $R_3$, and $R_4$ is independently a hydrogen or an alkyl group, and wherein the total number of carbons in the olefin is not more than twenty-two. Optionally, $R_1$, $R_2$, $R_3$, and $R_4$ can form a ring independently with each other to form a cyclic or bicyclic alkyl group. A preferred olefin for this invention is one wherein $R_1$, $R_2$, $R_3$, and $R_4$ are independently hydrogen or an alkyl group, and wherein the total number of carbons in the olefin is not more than nine.

By the term "sugar" is meant a five-carbon pentose sugar or a six-carbon hexose sugar.

By the term "acid catalyst" is meant a substance which has the ability to donate protons as defined by Brönsted, or a substance which can form a covalent bond with an atom, molecule or ion that has an unshared electron pair as defined by Lewis. Any known acid catalysts can be used for the process of the present invention. A further definition of acid catalysts and how to determine if a particular substance is acidic is explained in Tanabe, K., *Catalysis: Science and Technology*, Vol. 2, pg. 232–273, ed. Anderson, J. and Boudart, M., Springer-Verlag, N.Y., 1981.

By the term "biofuel" is meant either a 100% biodiesel or a mixture comprising biodiesel and regular petroleum-based diesel from a refinery. For example, B20 is a mixture of 20% biodiesel based on vegetable oil, and 80% regular diesel. Biodiesel is a product of esterification of oils such as palm, canola, tallow, corn, and soy, with methanol.

By the term "octane number" is meant an empirical rating of the anti-knock quality of a fuel. "Knock" is caused by secondary ignition of fuel unburned after normal spark ignition, which gives rise to a fast moving flame front in an automobile's engine cylinder. Pressure waves are setup, which vibrate against the cylinder walls giving rise to a "knocking" sound. This feature of fuel is undesirable because it accelerates wear in the engine bearings and causes overheating in the cylinders. The tendency of the fuel to knock increases as the compression ratio increases. Certain fuels have better anti-knock characteristics than others because of their molecular structure, branched structures having better characteristics. On the arbitrary octane scale, iso-octane ($C_8H_{18}$) is given an octane value of 100; n-heptane($C_7H_{16}$), is given a value of zero. The octane number of a fuel is determined by comparing its performance in a standard spark-ignition engine with the performance of various mixtures of iso-octane and n-heptane. The behavior of the fuel is carefully matched by a known mixture of iso-octane and n-heptane. The percentage of isooctane in this mixture is then taken as the octane number of the fuel.

The "cetane number" is used to evaluate fuels used in compression-ignition (diesel) engines and is analogous to octane number. Cetane (n-hexadecane, $C_{16}H_{34}$) is designated 100 and alpha-methyl-naphthalene($C_{11}H_{10}$) as zero, so that the cetane number of a fuel is the proportion of the cetane in the mixture of these having the same ignition delay after injection of the fuel as the test fuel.

The present invention relates to the use of esters with low water solubility as fuel additives. Described herein is a direct method of producing fuel additives from biomass, comprising a mixture of levulinate esters (used interchangeably herein with "levulinic acid esters") and formate esters (used interchangeably herein with "formic acid esters") for use as oxygenates. Besides being used as oxygenate additives for diesel fuel, gasoline fuel and biofuel, these esters can also be used as octane number-enhancing agents for gasoline, and as cetane number-enhancing agents in diesel fuels. The reaction mixture of esters of the present invention can also be directly used as 100% fuel. More specifically, the process of the present invention describes a direct method of producing ester-based fuel additives by the reaction of olefins with levulinic acid and formic acid. Formic acid is produced as a byproduct of acid hydrolysis of biomass to levulinic acid.

It had previously been believed that in order to produce a superior fuel additive, the formic acid byproduct has to be separated along with the carbon-based solid byproducts from the reaction mixture to form pure levulinic acid as a fuel additive. Subsequently, the levulinic acid would be used for its intended purpose. (See, for example, U.S. Pat. No. 5,608,105). However, the present invention teaches a process for obtaining a fuel additive from the mixture of levulinic acid and formic acid, by eliminating the purification step and using the formic acid byproduct in the process. Removing the formic acid byproduct from the levulinic acid is not necessary.

The process of the invention comprises the step of reacting the mixture of acids (levulinic acid and formic acid) with olefins such as ethylene, propylene, butenes, pentanes, etc. The process of the present invention offers two advantages: (1) formic acid removal to obtain pure levulinic acid is not necessitated, and (2) a mixture of levulinate ester and formate ester, obtained as a result of reaction with olefin has superior oxygenate values compared to pure levulinate ester.

For example, the oxygen content per unit weight of the 50/50 weight percent mixture of ethyl levulinate and ethyl formate is about 15% higher than that of pure ethyl levulinate.

In the conversion step of biomass to ester-based fuel additives, biomass is contacted with water and an acid catalyst, preferably under pressure at an elevated temperature. This basic process with modifications is described for example, in U.S. Pat. No. 5,608,105, U.S. Pat. No. 5,859, 263, and U.S. Pat. No. 6,054,611.

Cellulose in the biomass is converted to a six-carbon sugar. The six carbon sugar breaks up in presence of an acid into levulinic acid, formic acid, and water. Any hemicellulose in the biomass is converted into furfural and water. However, since the biomass can contain a mixture of cellulose and hemicellulose, generally, a mixture of levulinic acid, formic acid, furfural, water, and solid 'humus' material is obtained. The reaction generally results in a liquid phase and a solid phase. The solid material can be dispersed in the liquid phase of the reaction product.

Furfural, resulting from a five-carbon sugar, is immiscible with the liquid phase. Therefore, it is preferably removed using an appropriate liquid-liquid separation method such as decantation. The product of the above reaction, after the removal of furfural, consists of an acidified aqueous solution of levulinic acid, formic acid, and solid 'humus' material. The 'humus' material is dispersed in the liquid phase, or can settle at the bottom of the reaction vessel. The solid phase can be optionally separated from the liquid phase, using an appropriate solid-liquid separation method for example, sedimentation, filtration, centrifugation, spray drying, evaporation, decantation, thickening, or a combination of these techniques.

In the biomass conversion step of the process of the invention, a temperature range of from about 100° C. to about 300° C. is preferred. A temperature range of from about 200° C. to about 275° C. is further preferred. A pressure range of from about 0.69 MPa to about 13.8 MPa is preferably employed; a pressure range of from about 1.38 MPa to about 2.75 MPa being preferred.

In the next step of the reaction, an olefin is added to the filtrate obtained above, in the presence of an acid catalyst. Unreacted olefins used in excess in this step can be directly added to fuel without downgrading the fuel value as measured by octane number or cetane number.

A cis- and a trans-isomeric mixture of levulinate ester, and a cis- and a trans-isomeric mixture of formate ester may be formed in the above reaction.

Optionally, the olefins may be added in the presence of a water-immiscible hydrocarbon solvent. Water-immiscible solvents, which have been found to be particularly suitable in the process of the invention, include aromatic hydrocarbons, such as toluene, xylene, and ethyl benzene. Aliphatic hydrocarbons such as n-hexane, n-heptane, and iso-octane are also suitable. Also, in certain instances, water-immiscible materials such as cycloaliphatic hydrocarbons (e.g. cyclohexane) and pelargonic acid and the like, may also be used. In general, any material which is substantially water-immiscible and which will extract a good portion of the esters but will not extract appreciable quantities of the acid may be employed in this step of the process. Of these extractants, iso-octane is an especially suitable immiscible solvent as it is readily available, chemically inert, easily recovered, and can be used as an additive to the fuel. Solvent mixtures may also be used.

After the addition of the water-immiscible solvent, an aqueous phase and an organic phase are allowed to layer out and the two phases are separated for further processing, for example, by decantation.

As a result of this procedure, levulinic acid and formic acid are reactively extracted from the organic phase, as esters of levulinic acid and formic acid. The separated organic phase comprising the ester mixture and the organic solvent can be added as a fuel additive to hydrocarbon fuel.

Alternatively, the hydrocarbon phase from the above process can also be preferably distilled at atmospheric pressure to recover the immiscible solvent. The residue from this operation is distilled, preferably under vacuum, to yield the esters of levulinic acid and formic acid. In general, as the olefins react with the acids contained in the solution to form the alkyl esters thereof, the higher the temperature employed, the faster the reaction will proceed, so that it is generally preferred to conduct this reaction at a slightly elevated temperature in order to obtain maximum yield in the shortest time possible. A preferred temperature range is from about 0° C. to about 200° C.

The reaction of levulinic acid and formic acid with the olefins is effected in the presence of an acid catalyst in order to form the esters of levulinic acid and formic acid. In many instances, the mixture of acids to be treated will be found to contain sufficient acidic catalyst as spent acid, to provide the required amount of acid.

Acid catalysts that may be employed in the process of the invention include inorganic acids such as sulfuric acid, hydrochloric acid, and nitric acid, as well as mixtures thereof. Organic acids such as para-toluene sulfonic acid may also be used. Moreover, ion exchange resins in the acid form may also be employed. Hence, any type of acid catalyst known in the art may be employed.

Fluorinated sulfonic acid polymers can also be used as acid catalysts for the process of the present invention. These acids are partially or totally fluorinated hydrocarbon polymers containing pendant sulfonic acid groups, which may be partially or totally converted to the salt form. One particularly suitable fluorinated sulfonic acid polymer is Nafion® perfluorinated sulfonic acid polymer, (E.I. du Pont de Nemours and Company, Wilmington, Del.). One preferred form is Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton ($H^+$), or the metal salt form.

A soluble acid catalyst may also be used during the method of the invention. Suitable soluble acids include, those acid catalysts with a pKa less than about 4, preferably with a pKa less than about 2, including inorganic acids, organic sulfonic acids, heteropolyacids, perfluoroalkylsulfonic acids, and combinations thereof. Also suitable are metal salts of acids with pKa less than about 4, including metal sulfonates, metal sulfates, metal trifluoroacetates, metal triflates, and mixtures thereof, including mixtures of salts with their conjugate acids. Specific examples of suitable acids include sulfuric acid, fluorosulfonic acid, phosphoric acid, p-toluenesulfonic acid, benzenesulfonic acid, phosphotungtstic acid, phosphomolybdic acid, tri fluromethanesulfonic acid, 1,1,2,2-tetrafluroethanesulfonic acid, 1,2,3,2,3,3-hexapropanesulfonic acid, bismuth triflate, yttrium triflate, ytterbium triflate, neodymium triflate, lanthanum triflate, scandium triflate, zirconium triflate, and $Zn(BF_4)_2$.

The acid catalyst is preferably used in an amount of from 0.01% to 5% by weight of the reactants independently in each step of the reaction. A preferred range is 0.25% to 2.5% by weight of the reactants.

Heterogeneous acid catalysts can also be used during the process of the invention. Suitable heterogeneous acids are, for example, zeolites, CBV-3020 zeolite, fluorinated alumina, acid-treated silica, acid treated silica-alumina, acid treated clays, heterogeneous heteropolyacids and sulfated zirconia. The acid catalyst can also be selected from the group consisting of sulfuric acid-treated silica, sulfuric acid-treated silica-alumina, acid-treated titania, acid-treated zirconia, heteropolyacids supported on zirconia, heteropolyacids supported on titania, heteropolyacids supported on alumina, heteropolyacids supported on silica, and combinations thereof. Suitable heterogeneous acid catalysts include those having an $H_0$ of less than or equal to 2.

During formation of the esters, the aqueous phase and organic phase can be processed in any desirable manner to recover the valuable products contained therein. The aqueous phase contains water, any inorganic acid or catalytic components that may be present, as well as a very small amount of the organic acids, which were not esterified. This aqueous layer is most suitably processed by subjecting to distillation to remove the water fraction. Any inorganic acid or catalytic components will then be in concentrated form in the residue and may be used as desired or discarded. However, any other suitable processing technique may be employed.

The organic phase will be found to contain the water-immiscible solvent and the esters, and may be processed as desired. A suitable processing technique is to subject the organic phase to distillation by fractionation so as to separate the water-immiscible solvent as one fraction and the mixed esters contained therein as second or separate fractions. This ester mixture can then be used as a fuel additive. If the organic solvent is such that it could be used as an additive to fuel, for example, iso-octane, separation of the esters may not be required.

The process of the invention as described is directed to the batch method of production. The process can also be performed by a continuous method using a combination of reaction and extraction procedures. The continuous method requires the use of a series of esterifiers and extraction tanks. Thereby, a given feed material may be continuously esterified and extracted with the esterifying olefin and extractant solvent being continuously recycled as they are recovered.

In the continuous method, the olefins are mixed in an esterification zone with the acids necessary to obtain at least partial esterification to the point of equilibrium. Thereafter, this mixture is passed into the extraction zone where it is admixed with the water-immiscible extractant solvent, the mixing being preferably conducted under countercurrent conditions for good contact. In this zone, the extractant solvent continuously extracts the esters from the aqueous phase to the organic phase. Further, as this extractive procedure proceeds, the equilibrium of the mixture is upset so that the extraction causes the formation of more esters to the point that all the acids present are converted into their esters and extracted into the organic phase. This esterification/extraction technique therefore is effective to remove the acids in the form of their esters with the esters being transferred to the organic phase.

The resulting mixture is then passed to a separation or settling zone where the layers are separated as an aqueous phase containing any water-soluble impurities, and an organic phase containing the esters in the extractant solvent. The aqueous phase can then be distilled to remove the excess olefin and the olefin is recycled to the esterification zone for further reaction with additional acid feed and makeup olefin. Any acid catalyst present may also be recovered and recycled to the esterification chamber. Moreover, the organic phase is subsequently distilled to remove the extractant solvent and the latter is recycled to the extraction chamber.

The process of the present invention may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA).

For the step involving the formation of the esters, a temperature range of from about 25° C. to about 200° C. is preferred for the processes of the invention. A temperature range of from about 50° C. to about 150° C. is further preferred. A pressure range of from about 0.69 MPa to about 6.9 MPa is employed for this step of the process of the invention. A pressure range of from about 1.00 MPa to about 3.45 MPa is preferred.

As liquid organic based fuels for use in internal combustion engines, the reaction mixture containing levulinic acid esters and formic acid esters as obtained from the process of the invention, can be used in the range of from about 1% to about 99% by volume, as additive to gasoline, diesel, or biofuel. A preferred range is from about 1% to about 90% by volume. A more preferred range is from about 1% to about 50% by volume. A further preferred range is from about 1% to about 20% by volume. Moreover, the reaction mixtures of esters of this invention can also be used as 100% fuel.

The mixture of esters prepared according to the process of the invention contains significantly higher oxygen content than MTBE. Therefore, a lesser amount of esters is required in order to meet the various clean fuel programs' oxygen requirements for gasoline. Also, the mixture of esters made by the process of the invention in general has lower vapor pressures than MTBE. This indicates that the esters will also have a lower Reid Vapor Pressure (RVP) than MTBE. The addition to gasoline of esters that have low RVP is beneficial because it enables the addition of high RVP paraffins, such as butane, isobutane and isopentane, in order to meet the regulated RVP requirements of gasoline. Previously reported blending octane numbers show that the esters made by the process of the invention can also act as octane-enhancing agents for gasoline. Table 1 herein demonstrates comparative data for fuel additive characteristics of the reaction mixture of the invention as compared to MTBE. The information for Table 1 was obtained from the following references: [1] Design Institute for Physical Property Data (DIPPR)®, Project 801, Sponsor Release January 2002. [2] Alternatives to Traditional Transportation Fuels: An Overview. Report DOE/EIA-0585/O (June 1994). [3] Jungbluth et al. Liquid Fuels. International Patent Application WO 94/21753 (1994).

EXAMPLES

The invention is further demonstrated by the following Examples set forth.

Example 1

Levulinic Acid and Formic Acid Conversion to Levulinate and Formate Esters by Reaction with Olefins A 5 cc autoclave is charged with 2 cc of an aqueous solution containing 2 mmoles of levulinic acid and 2 mmoles of formic acid. 5 wt. % sulfuric acid is added as a catalyst. The reactor is pressurized to 0.69 MPa with 1-butene and heated to 100° C. for 2 hours while maintaining a constant pressure of 1-butene. After cooling, the organic phase is separated. A mixture of butyl formate and butyl levulinate is formed as product.

Example 2

Levulinic Acid and Formic Acid Conversion to Levulinate and Formate Esters by Reaction with Olefins in the Presence of a Hydrocarbon Phase A 5 cc autoclave is charged with 1 cc of iso-octane and 1 cc of an aqueous solution containing 2 mmoles of levulinic acid and 2 mmoles of formic acid. 5 wt. % sulfuric acid is added as a catalyst. The reactor is pressurized to 0.69 MPa with 1-butene and heated to 100° C. for 2 hours while maintaining a constant pressure of 1-butene. After cooling, the organic phase is separated. A mixture of butyl formate and butyl levulinate is formed as product.

Example 3

Levulinic Acid and Formic Acid Conversion to Levulinate and Formate Esters by Reaction with Olefins in the Presence of a Hydrocarbon Phase A 5 cc autoclave is charged with 1 cc of heptane and 1 cc of an aqueous solution containing 2 mmoles of levulinic acid and 2 mmoles of formic acid. 5 wt. % sulfuric acid is added as a catalyst. The reactor is pressurized to 0.69 MPa with 1-butene and heated to 150° C. for 0.5 hours while maintaining a constant pressure of isobutene. After cooling, the organic phase is separated. A mixture of butyl formate and butyl levulinate is formed as product.

Example 4

Levulinic Acid and Formic Acid Conversion to Levulinate and Formate Esters by Reaction with Olefins in the Presence of a Hydrocarbon Phase A 5 cc autoclave is charged with 1 cc of iso-octane and 1 cc of an aqueous solution containing 2 mmoles of levulinic acid and 2 mmoles of formic acid. 5 wt. % sulfuric acid is added as a catalyst. The reactor is pressurized to 0.69 MPa with 1-pentene and heated to 75° C. for 5 hours while maintaining a constant pressure of 1-butene. After cooling, the organic phase is separated. A mixture of pentyl formate and pentyl levulinate is formed as product.

Example 5

Levulinic Acid and Formic Acid Conversion to Levulinate and Formate Esters by Reaction with Olefins A 5 cc autoclave is charged with 2 cc of an aqueous solution containing 2 mmoles of levulinic acid and 0.5 mmoles of formic acid. 2 wt. % triflic acid is added as a catalyst. The reactor is pressurized to 0.69 MPa with 1-butene and heated to 100° C. for 0.5 hours while maintaining a constant pressure of 1-butene. After cooling, the organic phase is separated. A mixture of butyl formate and butyl levulinate is formed as product.

Example 6

Levulinic Acid and Formic Acid Conversion to Levulinate and Formate Esters by Reaction with Olefins A 5 cc autoclave is charged with 2 cc of an aqueous solution containing 0.5 mmoles of levulinic acid and 2 mmoles of formic acid. 15 wt. % ZSM-5 zeolite is added as a catalyst. The reactor is pressurized to 0.69 MPa with 1-butene and heated to 100° C. for 4 hours while maintaining a constant pressure of 1-butene. After cooling, the organic phase is separated. A mixture of butyl formate and butyl levulinate is formed as product.

Example 7

Levulinic Acid and Formic Acid Conversion to Levulinate and Formate Esters by Reaction with Olefins A 5 cc autoclave is charged with 2 cc of an aqueous solution containing 2 mmoles of levulinic acid and 0.2 mmoles of formic acid. 3 wt. % toluene sulfonic acid is added as a catalyst. The reactor is pressurized to 0.69 MPa with 1-hexene and heated to 100° C. for 2 hours while maintaining a constant pressure of 1-hexene. After cooling, the organic phase is separated. A mixture of hexyl formate and hexyl levulinate is formed as product.

What is claimed is:

1. A process for preparing a mixture comprising levulinic acid esters and formic acid esters from biomass, the process comprising the steps of:
   (a) contacting the biomass with water in the presence of a first acid catalyst to form a first reaction mixture comprising levulinic acid, formic acid and furfural, the first reaction mixture having a liquid phase and, optionally, a solid phase;
   (b) optionally, separating the liquid phase from the solid phase of the first reaction mixture to form a second reaction mixture;
   (c) removing the furfural from the first reaction mixture or the second reaction mixture to form a third reaction mixture;
   (d) contacting the first reaction mixture, the second reaction mixture, or the third reaction mixture with at least one olefin, optionally, in the presence of a second acid catalyst, to produce a fourth reaction mixture, the fourth reaction mixture having an organic phase and an aqueous phase;

(e) separating the organic phase containing levulinic acid esters and formic acid esters from the aqueous phase of the fourth reaction mixture; and (f) optionally, isolating the mixture comprising levulinic acid esters and formic acid esters from the organic phase of step (e).

2. The process of claim 1, wherein the first acid catalyst or the second acid catalyst, independently, is a soluble acid catalyst with a pKa less than 4, or a metal salt thereof.

3. The process of claim 1, wherein the first acid catalyst or the second acid catalyst, independently, is a soluble acid catalyst with a pKa less than 2, or a metal salt thereof.

4. The process of claim 1, wherein the first acid catalyst and the second acid catalyst, independently, are selected from the group consisting of inorganic acids, organic sulfonic acids, heteropolyacids, perfluoroalkyl sulfonic acids, metal salts thereof, mixtures or metal salts, and combinations thereof.

5. The process of claim 1, wherein the first acid catalyst and the second acid catalyst, independently, are selected from the group consisting of zeolites, CBV-3020 zeolite, fluorinated alumina, acid-treated silica, acid-treated silica-alumina, acid-treated titania, acid-treated zirconia, heteropolyacids supported on zirconia, titania, alumina, or silica; and combinations thereof.

6. The process of claim 1, wherein the first acid catalyst and the second acid catalyst, independently, are selected from the group consisting of metal sulfonates, metal sulfates, metal trifluoroacetates, metal triflates, and mixtures thereof; mixtures of salts with their conjugate acids, $Zn(BF_4)_2$, and combinations thereof.

7. The process of claim 1, wherein the first acid catalyst and the second acid catalyst, independently, are selected from the group consisting of sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluorethanesulfonic acid, 1,1,1,2,3,4-hexafluorpropanesulfonic acid, bismuth triflate, yttrium triflate, ytterbium triflate, neodymium triflate, lanthanum triflate, scandium triflate, zirconium triflate, and combinations thereof.

8. The process of claim 1, wherein the first acid catalyst and the second acid catalyst, independently, are used in an amount of from 0.01% to 5% by weight of the reactants.

9. The process of claim 1, wherein the first acid catalyst and the second acid catalyst, independently, are used in an amount of from 0.25% to 2.5% by weight of the reactants.

10. The process of claim 1, wherein in step (b), the solid phase is separated from the liquid phase by a liquid-solid separation method selected from a group consisting of sedimentation, filtration, centrifugation, decantation, thickening, spray drying, evaporation, and combinations thereof.

11. The process of claim 1, wherein in step (c), the furfural is separated by a liquid-liquid separation method.

12. The process of claim 1, wherein the olefin is selected from the group consisting of compounds having formula (I), wherein $R_1$, $R_2$, $R_3$, and $R_4$ are independently hydrogen or an alkyl group, and optionally, $R_1$, $R_2$, $R_3$, and $R_4$ form a ring independently with each other to form a cyclic or bicyclic alkyl group, and wherein the total number of carbons in the compound is not more than twenty two

13. The process of claim 1, wherein the olefin is selected from the group consisting of compounds having formula (I), wherein $R_1$, $R_2$, $R_3$, and $R_4$ are independently hydrogen or an alkyl group, and optionally, $R_1$, $R_2$, $R_3$, and $R_4$ form a ring independently with each other to form a cyclic or bicyclic alkyl group, and wherein the total number of carbons in the compound is less than nine

14. The process of claim 1, wherein in step (d), said olefin is contacted with said liquid phase in the presence of at least one water-immiscible solvent.

15. The process of claim 1, wherein in step (d), the organic phase and the aqueous phase are separated by a process selected from a group consisting of reactive extraction, liquid-liquid extraction, distillation, absorption, membrane separation, decantation, and combinations thereof.

16. A process for manufacturing a fuel additive, the process comprising the process of claim 1.

17. A process for manufacturing a gasoline, a diesel fuel or a biofuel the process comprising the process of claim 1.

* * * * *